US007884077B2

(12) United States Patent
Cohen et al.

(10) Patent No.: US 7,884,077 B2
(45) Date of Patent: Feb. 8, 2011

(54) METHODS FOR THE TREATMENT OF MOOD DISORDERS

(75) Inventors: Bruce M. Cohen, Lexington, MA (US); Beth L. Murphy, Arlington, MA (US)

(73) Assignee: The McLean Hospital Corporation, Belmont, MA (US)

( * ) Notice: Subject to any disclaimer, the term of this patent is extended or adjusted under 35 U.S.C. 154(b) by 0 days.

(21) Appl. No.: 12/229,841

(22) Filed: Aug. 27, 2008

(65) Prior Publication Data

US 2009/0048177 A1 Feb. 19, 2009

Related U.S. Application Data

(63) Continuation-in-part of application No. PCT/US2007/024683, filed on Nov. 30, 2007, and a continuation-in-part of application No. PCT/US2006/007833, filed on Mar. 3, 2006.

(60) Provisional application No. 60/861,938, filed on Nov. 30, 2006.

(51) Int. Cl.
*A61K 31/55* (2006.01)
*A61K 31/5513* (2006.01)

(52) U.S. Cl. .................... 514/18.4; 514/18.1; 514/18.3; 514/186

(58) Field of Classification Search .................... None
See application file for complete search history.

(56) References Cited

U.S. PATENT DOCUMENTS

| 5,817,665 | A | * | 10/1998 | Dante | 514/282 |
| 5,856,332 | A | * | 1/1999 | Dante | 514/282 |
| 2004/0180916 | A1 | | 9/2004 | Levine | |
| 2006/0052439 | A1 | * | 3/2006 | Beguin et al. | 514/455 |
| 2007/0213394 | A1 | * | 9/2007 | Beguin et al. | 514/455 |

FOREIGN PATENT DOCUMENTS

| WO | WO 2005/089745 | 9/2005 |
| WO | WO 2008/066916 | 6/2008 |
| WO | WO 2010/075045 | 7/2010 |

OTHER PUBLICATIONS

Bipolar disorder from Merck manual, pp. 1-5. Accessed Aug. 6, 2009.*
Dynorphin A (1-17) from http://www.anaspec.com/products/product.asp?id=32272, p. 1. Accessed Aug. 6, 2009.*
Hiramatsu M, Hoshino T, "Improvement of memory impairment by (+)- and (−)-pentazocine via sigma, but not kappa opioid receptors," Brain Research, 2005, 1057: 72-80.*
Talwin Nx from http://www.rxlist.com/talwin-nx-drug.htm, pp. 1-3. Accessed Jan. 19, 2010.*
Carlezon et al., Kappa-opioid Ligands in the Study and Treatment of Mood Disorders, Pharmacol. And Ther (2009), doi:10.1016/j.pharmthera.2009.05.008.
Cohen et al., The Effects of Pentazocine, a Kappa Agonist, in Patients with Mania, Int. J. Neuropsycopharmacology 11:243-247 (2007).
Murphy et al., "The Effects of Pentazocine, A Kappa Agonist, in Mania," Abstracts from the ACNP (American College of Neuropsychopharmacology) 45th Annual Meeting. 2006. Hollywood, Florida, USA.
National Institute of Health Clinical Trial: "Effects of Pentazocine on Manic Symptoms," http://clinicaltrials.gov/ct/show/NCT00125931, Mar. 16, 2006.
Zhu et al., Activation of the Cloned Human Kappa Opioid Receptor by Agonists Enhances [$^{35}$S]GTP$\gamma$S Binding to Membranes: Determination of Potencies and Efficacies of Ligands[1], J. of Pharm. 282:676-684 (1997).
International Preliminary Report on Patentability for PCT/US2007/24683, issued Jun. 3, 2009.
Written Opinion of the International Searching Authority for PCT/US2007/24683, completed Mar. 5, 2008.

* cited by examiner

*Primary Examiner*—Julie Ha
(74) *Attorney, Agent, or Firm*—Clark & Elbing LLP

(57) ABSTRACT

The invention features methods of treating mood disorders, such as manic disorders, and stabilizing moods by administering a kappa agonist or partial agonist to a subject in need thereof.

6 Claims, 3 Drawing Sheets

METHODS FOR THE TREATMENT OF MOOD DISORDERS

CROSS-REFERENCE TO RELATED APPLICATIONS

This application is a Continuation-In-Part of PCT Application No. PCT/U.S.07/024,683, filed Nov. 30, 2007, which claims the benefit of U.S. Provisional Application No. 60/861,938, filed Nov. 30, 2006, and this application is also a Continuation-In-Part of PCT Application No. PCT/US06/07833, filed Mar. 3, 2006. Each of the above-referenced applications are incorporated herein by reference.

BACKGROUND OF THE INVENTION

The invention relates to the treatment of mood disorders.

Opiates have a long history of treating mood disorders. In the classical world, records indicate that opium was used as a treatment for both 'melancholia' and 'mania' (Weber et al., Int. Clin. Psychopharmacol. 3:255-266 (1988)). It has also been long noted that opiates can have euphorigenic effects. However, as awareness of opiate addiction increased, the use of potentially-addicting opiate treatment for mood disorders fell out of favor. Interest in opiates as treatments for mood disorders has increased again, as a better understanding of opiate receptor subtypes and their individual involvement in mood and addiction developed.

As in many other neurotransmitter systems, the opiate system involves multiple receptor subtypes. Three kinds of opioid receptors have been identified; mu, kappa, and delta. The best-studied of these receptors are the mu receptors, which are preferentially bound by morphine and related compounds. The endogenous ligands for these receptors are endorphins. Mu receptors are concentrated in regions which mediate analgesic pathways. These receptors are also located in regions which are critical for the reinforcing effects of opiates. Kappa opiate receptors (KOR) are also found in areas mediating addiction and reward. In contrast to many opiate-receptor agonists, activation of KOR is not highly addictive, and co-administration may decrease the addictive potential of other substances (Shippenberg et al., Ann N Y Acad Sci. 937: 50-73 (2001)). The endogenous ligand for KOR is dynorphin.

As their location would suggest, studies indicate that mood and reward systems are modulated by the opiate systems (see Todtenkopf et al., Psychopharmacology 172:463-470 (2004) and Pickar et al., Biol. Psychiatry 17:1243-1276 (1982)). Changes in cAMP response element binding protein (CREB) appear to mediate mood and affect animal models of reward and depression (Pliakas et al., J. Neurosci. 21:7397-7403 (2001)). Interestingly, CREB modulates the expression of dynorphin, an endogenous ligand of KOR (see Todtenkopf et al., Psychopharmacology 172:463-470 (2004) and Carlezon et al., Science 282:2272-2275 (1988)).

Therapeutic alternatives for bipolar mania include mood stabilizers such as valproic acid, lithium, and carbamezapine. Alternatives also include neuroleptics such as haldol, trilafon, thorazine, zyprexa, risperdal, seroquel, and clozaril. In addition, benzodiazepines and electro-convulsive treatment may be used to treat bipolar mania. Neuroloeptics have been shown to increase the activity of neurons which produce dynorphin (Ma et al, Neuroscience 121:991-998 (2003)).

There is a need for new therapies for the treatment of mood disorders, such as bipolar mania, which provide a more rapid amelioration of manic symptoms. The profile and actions of the kappa opioid system make drugs that target this system particularly promising as a treatment modality, with relatively low risk of addictive properties.

SUMMARY OF THE INVENTION

The invention is based on the discovery that modulation of activity at kappa opioid receptors can be useful for the treatment of mood disorders. For example, compounds exhibiting agonist or partial agonist activity at kappa receptors can be useful for the treatment of bipolar disorder, e.g., as mood stabilizers, and for the treatment of the manic phase of bipolar disorder, among other conditions.

In a first aspect, the invention features a method for treating mania in a human subject in need thereof by administering an effective amount of a kappa receptor agonist or partial agonist. Kappa receptor agonists and partial agonists can be particularly useful for treating mania associated with bipolar disorder, acute mania, and chronic mania. The mania can occur in a single episode or be recurring.

The invention further features a method for treating bipolar disorder in a human subject in need thereof by administering an effective amount of a kappa receptor agonist or partial agonist.

The invention also features a method for stabilizing the mood of a human subject diagnosed with a mood disorder by administering an effective amount of a kappa receptor partial agonist.

The invention further features a kit comprising (i) a compound having kappa receptor agonist or partial agonist activity, and (ii) instructions for the administration of the compound for the treatment of mania.

The invention also features a kit comprising (i) a compound having kappa receptor agonist or partial agonist activity, and (ii) instructions for the administration of the compound for the treatment of bipolar disorder.

The invention further features a kit comprising (i) a compound having kappa receptor agonist or partial agonist activity, and (ii) instructions for the administration of the compound for stabilizing the mood of a subject.

For any of the above methods and kits of the invention the kappa receptor agonist or partial agonist can be selected from dynorphin A 1-17, ethylketocyclazocine, U50,488H, tifluadom, β-funaltrexamine, nalmefine, nalorphine, pentazocine, and substantially pure enantiomers thereof. Desirably, the kappa receptor agonist or partial agonist is pentazocine, either administered as a racemate, or as a substantially pure enantiomer as (−) pentazocine or (+) pentazocine.

The kappa receptor partial agonists and full agonists can be administered systemically, including, for example, by intravenous, intramuscular, or subcutaneous injection, orally, or by topical or transdermal application, provided that the agent is capable of penetrating the blood-brain barrier sufficiently to be effective. Alternatively, the kappa-selective compounds can be centrally administered using, for example, by an intrathecal, intracerebroventricular, or intraparenchemal injection.

By "kappa receptor partial agonist" is meant any chemical compound which has affinity for the kappa opioid receptor and agonist activity, but produces only a partial (i.e., sub-maximal) response of between 15% and 85% in comparison to dynorphin A, an endogenous neurotransmitter of the kappa opioid receptor.

By "kappa receptor agonist" (KOR) is meant any chemical compound which has affinity for the kappa opioid receptor and agonist activity, and produces at least 85% of the maximal response in comparison to dynorphin A, an endogenous neurotransmitter of the kappa opioid receptor.

The term "administration" or "administering" refers to a method of giving a dosage of a pharmaceutical composition to a patient, where the method is, e.g., topical, transdermal, oral, intravenous, intraperitoneal, intracerebroventricular, intrathecal, or intramuscular. The preferred method of administration can vary depending on various factors, e.g., the components of the pharmaceutical composition, site of administration, and severity of the symptoms being treated.

By "effective amount" is meant an amount of a compound of the invention which has a therapeutic effect, e.g., which prevents, reduces, or eliminates the mania, or mood fluctuations. This amount, an effective amount, can be routinely determined by one of skill in the art, by animal testing and/or clinical testing, and will vary, depending on several factors, such as the particular disorder to be treated and the particular compound of the invention used. This amount can further depend upon the subject's weight, sex, age and medical history.

As used herein, the term "substantially pure" refers to a composition containing a single predominant isomer of a kappa receptor partial agonist or full agonist possessing one or more chiral centers, wherein the amount of any other single isomer (i.e., enantiomer or diastereomer) of the predominant isomer is less than 1%, 0.5%, 0.1%, 0.05%, or even 0.01% of the mass of the predominant isomer present in the composition.

Other features and advantages of the invention will be apparent from the following Detailed Description, the drawings, and the claims.

DETAILED DESCRIPTION

Figure 1:
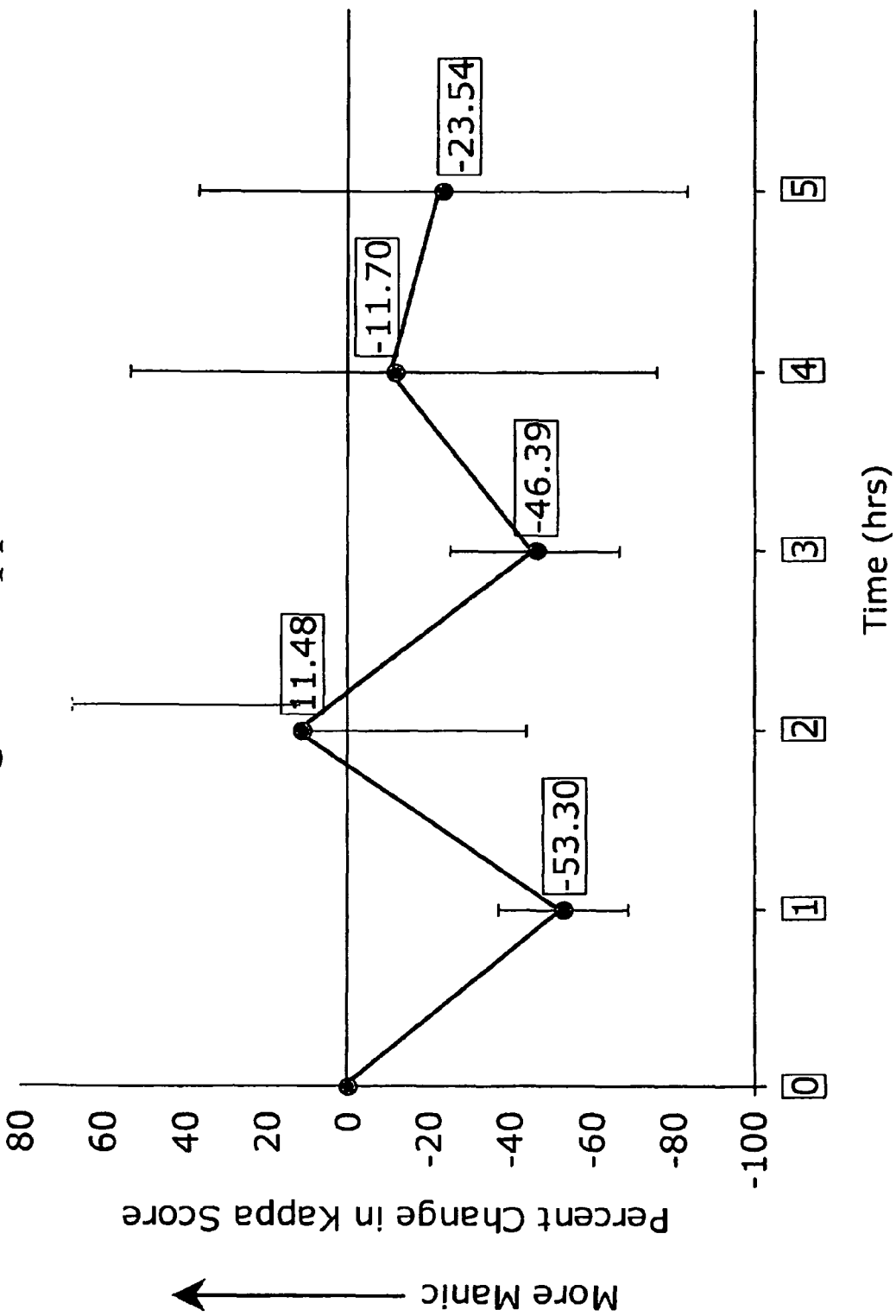
FIG. 1 is a graph showing the effect of pentazocine on the manic symptoms of human subjects who have been diagnosed with bipolar disorder and are acutely manic. Oral pentazocine was administered as Talwin Nx, which contains 50 mg pentazocine with 0.5 mg naloxone. Following pentazocine administration at time 0, manic symptoms decreased (F=3.69, df=5, p=0.01). At one hour after dosing, the mean change in total manic symptom ratings from baseline decreased of 44%. The mean change in total manic symptom ratings fell 41% between hour 2, when the second dose was given, and hour 3.

The invention features methods of treating mood disorders, such as manic disorders, and stabilizing moods by administering a kappa agonist or partial agonist to a subject in need thereof.

Assays

Compounds can be assayed to determine whether they have affinity and efficacy for kappa receptors, and thus are useful in the methods of the invention.

To determine their affinity for specific opioid receptors, the compounds described herein can be characterized in radioligand receptor binding assays, using ligands that are specific for the mu, delta and kappa receptors. For example, the binding assays may utilize guinea pig brain membranes or stably transfected Chinese Hamster Ovary (CHO) cells expressing each of the three opioid receptors, as described in Example 1.

To determine their efficacy (e.g., agonist, partial agonist, antagonist) at a specific opioid receptor, compounds can be characterized by [$^{35}$S]GTPγS binding assay, as described in Example 2.

Mania-like symptoms can be induced in rodents by the administration of psychomotor stimulant drugs such as cocaine or amphetamine. Psychostimulants produce a range of behaviors in animals that appear similar to mania, including hyperactivity, heightened sensory awareness and alertness, and changes in sleep patterns. Psychostimulant—induced hyperactivity is mediated by increased dopaminergic transmission in striatal regions. Based on this information, psychostimulant—induced hyperactivity in rodents has become a standard model for the screening of antimanic drugs. The mania-like effects of these psychomotor stimulants can be studied in behavioral assays that quantify locomotor activity ("open field activity") or the function of brain reward systems ("place conditioning" or "intracranial self-stimulation" (ICSS)) (see Example 3). The antimanic-like effects of a compound can be identified by its ability to reduce, attenuate, or block the stimulant or rewarding effects of cocaine or amphetamine in these assays. For further details see, for example, Einat and Belmaker Animal models of bipolar disorder: From a single episode to progressive cycling models; In: "Contemporary Issues in Modeling Psychopathology" Myslobodsky M, Weiner I (Eds.), 2000; London: Kluver Academic, New York, pp 165-179.

Therapy

Kappa agonists and partial agonists can be administered for the treatment of any psychologic or psychiatric disorder having symptoms that include abnormalities of mood or emotion, which are amenable to treatment according to the present methods. For example, kappa agonists and partial agonists can be administered to treat disorders of mood, including, without limitation, Bipolar Disorder, Schizoaffective Disorder, Schizophrenia and other psychotic disorders, Anxiety Disorders, Panic Disorder, Traumatic Stress Disorders, Phobic Disorders, and Personality Disorders with abnormal mood, such as Borderline Personality Disorder, Schizoid and Schizotypal Disorders. For example, compounds having partial agonist activity at kappa opioid receptors are useful as mood stabilizers for the treatment of, for example, bipolar disorder; and compounds having agonist activity at kappa opioid receptors are useful for the treatment of mania.

Using the methods of the invention, kappa agonists or partial agonists may be administered with a pharmaceutically acceptable diluent, carrier, or excipient, in unit dosage form. Administration may be transdermal, parenteral, intravenous, intra-arterial, subcutaneous, intramuscular, intracranial, intraorbital, ophthalmic, intraventricular, intracapsular, intraspinal, intracisternal, intraperitoneal, intracerebroventricular, intrathecal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycolate and deoxycholate, or may be oily solutions for administration in the form of nasal drops, or as a gel. The concentration of the compound in the formulation will vary depending upon a number of factors, including the dosage of the drug to be administered, and the route of administration.

The kappa agonist or partial agonist may be optionally administered as a pharmaceutically acceptable salt, such as non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid, phosphoric acid, or the like. Metal complexes include calcium, zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose (LD50) to median effective dose (ED50)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided as chewable tablets, or as hard gelatin capsules wherein the active ingredient is mixed with an inert solid diluent, or as soft gelatin capsules wherein the active ingredient is mixed with water or an oil medium.

The formulations can be administered to patients in therapeutically effective amounts. For example, an amount is administered which prevents, reduces, or eliminates the mania or mood fluctuations. Typical dose ranges are from about 0.001 µg/kg to about 2 mg/kg of body weight per day. Desirably, a dose of between 0.001 µg/kg and 1 mg/kg of body weight, or 0.005 µg/kg and 0.5 mg/kg of body weight, is administered. The exemplary dosage of drug to be administered is likely to depend on such variables as the type and extent of the condition, the overall health status of the particular patient, the formulation of the compound, and its route of administration. Standard clinical trials may be used to optimize the dose and dosing frequency for any particular compound.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLE 1

Radioligand Binding Assays

Compounds can be characterized in radioligand receptor binding assays, using ligands that are specific for the mu, delta and kappa receptors. The binding assays may utilize guinea pig brain membranes or stably transfected Chinese Hamster Ovary (CHO) cells expressing each of the three opioid receptors. Membranes can be isolated from CHO cells that stably express either the human mu, delta or kappa opioid receptors. At approximately 80% confluence, the cells are harvested by the use of a cell scraper. The cells and media from the plates are centrifuged at 200×g for 10 mm at 4° C.; resuspended in 50 mM Tris-HCl, pH 7.5; homogenized by the use of a Polytron; centrifuged at 48,000×g for 20 mm at 4° C.; and resuspended in 50 mM Tris-HCl, pH 7.5, at a protein concentration of 5-10 mg/ml, as determined by the Bradford method. The membranes are stored frozen, at −80° C. until use.

Cell membranes are incubated at 25° C. with the radiolabeled ligands in a final volume of 1 ml of 50 mM Tris-HCl, pH 7.5. Incubation times of 60 minutes are used for the mu-selective peptide [$^3$H]DAMGO and the kappa-selective ligand [$^3$H]Diprenorphine, and 4 hours of incubation for the delta-selective antagonist [$^3$H]naltrindole. Nonspecific binding is measured by inclusion of 1 µM naloxone. The binding can be terminated by filtering the samples through Schleicher & Scheull No. 32 glass fiber filters using a Brandel 48-well cell harvester. The filters are subsequently washed three times with 3 mL of cold 50 mM Tris-HCl, pH 7.5, and can be counted in 2 ml of Ecoscint A scintillation fluid. For [$^3$H] Diprenorphine binding, the filters are soaked in 0.1% polyethylenimine for at least 30 minutes before use. $IC_{50}$ values can be calculated by a least squares fit to a logarithm-probit analysis. Ki values of unlabeled compounds are calculated from the equation Ki=($IC_{50}$)/1=S where S=(concentration of radioligand)/(Kd of radioligand). Cheng and Prusoff, *Biochem. Pharmacol.* 22:3099 (1973). Alternatively, guinea pig brain membranes can be prepared and used as previously described in Neumeyer, et al., *J. Med. Chem.* 43:114 (2000). For further details see Huang et al., *J. Pharmacol. Exp. Ther.* 297:688 (2001); and Zhu et al., *J. Pharmacol. Exp. Ther.* 282:676 (1997). Other buffers may be used in the binding assay.

EXAMPLE 2

[$^{35}$S]GTPγS Binding Assays

Membranes from the CHO cell lines, expressing either the mu, delta or kappa receptor, are incubated with 12 concentrations of each compound for 60 minutes at 30° C. in a final volume of 0.5 ml of assay buffer (50 mM Tris-HCl, 3 mM $MgCl_2$, 0.2 mM EGTA, 100 mM NaCl, pH 7.5) containing 3 μM GDP and 0.08 nM [$^{35}$S]GTPγS. Basal binding can be determined in the presence of GDP and the absence of test compounds, and nonspecific binding can be determined by including 10 μM unlabeled [$^{35}$S]GTPγS. The incubation can be terminated by filtration under vacuum through glass fiber filters, followed by three washes with 3 ml ice-cold 50 mM Tris-HCl, pH 7.5. Samples can be allowed to equilibrate overnight and can be counted in 2 ml Ecoscint A scintillation fluid for 2 minutes in a liquid scintillation counter.

For [$^{35}$S]GTPγS binding assays, percent stimulation of [$^{35}$S]GTPγS binding is defined as [(stimulated binding-basal binding) basal binding]×100. Percent stimulation is plotted as a function of compound concentration (log scale), and $EC_{50}$ and $E_{max}$ values are determined by linear regression analysis. All data is compared across conditions using ANOVA and non-paired two-tailed Student's tests. For further details see Huang et al., *J. Pharmacol. Exp. Ther.* 297:688 (2001); and Zhu et al., *J. Pharmacol. Exp. Ther.* 282:676 (1997).

EXAMPLE 3

Intracranial Self-Stimulation (ICSS)

Intracranial self-stimulation (ICSS) is highly sensitive to the function of brain reward systems. In this assay, rodents respond to self-administer rewarding electrical stimulation through electrodes implanted within the limbic system. Changes in the rewarding efficacy of the stimulation shift the rate-frequency functions: leftward shifts (reflecting decreases in ICSS thresholds) imply that the stimulation is more rewarding as a result of a treatment, whereas rightward shifts (reflecting increases in thresholds) imply that it is less rewarding. The effects of many types of treatments on ICSS have been described. Most drugs of abuse decrease the amount of stimulation required to sustain responding: this is indicated by leftward shifts in rate-frequency functions and decreased ICSS thresholds. Conversely, agents that block drug reward (dopamine or kappa-opioid receptor agonists) increase the amount of stimulation required to sustain responding: this is indicated by rightward shifts in rate-frequency functions, and increased ICSS thresholds. Thus ICSS is sensitive to manipulations that increase or decrease reward.

Considering that mania is typically associated with increases in reward-driven behavior, the ICSS test may be a reasonable model of mania. Thus drugs that reduce the rewarding effects of the electrical stimulation may have some efficacy in the treatment of mania or related states.

EXAMPLE 4

Clinical Studies Using the Kappa Agonist Pentazocine

Opiates, which largely target mu opiate receptors, have been given in the past to patients with bipolar disorder, but specific agonists of KOR have not been tested in patients with mania. It is not known what sensitivity patients with mania would have to the mood altering or psychotomimetic effects of such agents.

No specific kappa agonist is currently approved for human use. However, the analgesic agent pentazocine is predominantly active at KOR, at which it is a partial agonist (Zhu et al., 1997). It has lower affinity and weaker effects at mu opiate receptors and sigma receptors (Bidlack et al., 2000). In a first trial, we tested whether pentazocine would be well tolerated and might have mood lowering effects in patients with mania without causing unwarranted side effects.

Subjects and Design

A trial study was conducted to determine the effect of pentazocine on the mood of human subjects who have been diagnosed with bipolar disorder and are acutely manic. Ten subjects (7 male and 3 female) between the ages of 18 and 65 were enrolled in the study. All subjects were admitted to the hospital with a primary diagnosis of bipolar mania by DSMIV criteria. On initial evaluation, all subjects had a Young Mania Rating Scale (YMRS) score of greater than or equal to 14. Subjects with a current history of substance abuse or a recent history of opiate dependence were excluded. All subjects were deemed competent to give informed consent by non-study physicians. After complete description of the study to the subjects, written informed consent was obtained.

The current study was undertaken in full compliance with federal requirements and with institutional review board approval. The study was designed as an open-label cumulative-dosing trial.

Treatment

The three-day study consisted of pre-treatment, treatment, and post-treatment days with subjects rated in the morning on all three days and multiple times on the day of treatment. On the treatment day, an initial 50 mg of pentazocine was given by mouth. A second dose was given two hours following the initial dose. Pentazocine was given as Talwin Nx (Sanofi-Synthlabo), consisting of 50 mg dose pentazocine with 0.5 mg naloxone (naloxone is added to limit the intra-venous abuse potential of this drug but is not absorbed when given by oral administration as used here).

Assessment of manic symptoms by YMRS were made daily at the same time in the morning on all three days of the study. As the YMRS was designed to reflect the past 48 hours, it is not sensitive to acute symptomatic change (IsHak et al, 2002) YMRS and DSMIV criteria were used as the basis for constructing a scale to detect acute changes in manic symptoms (The Mania Acute Change Scale or MACS). The MACS shows a high correlation with the YMRS (r=0.81, F=118.0, p<0.01). The MACS scale is available online at www.mcleanhospital.org. The MACS, which includes items from the YMRS and a brief assessment of dysphoria/depression was given along with the YMRS in the morning on all three days of the study. In addition, the MACS was given hourly for 6 hours starting with the first dose of pentazocine. All investigator ratings were performed by investigator Beth Murphy, M. D., Ph.D. A self-rating scale designed to assess manic symptoms and medication side effects was completed by subjects whenever the MACS was given. Staff reports were reviewed, with special note of the duration of sleep and whether any 'pro re nata' (PRN) medications were required. Data were analyzed using a repeated measures ANOVA (SPSS 14.0).

Results

Administration of pentazocine was well-tolerated. All enrolled subjects completed the protocol. No subject experienced significant side effects by clinician ratings or self-report.

All subjects experienced an improvement in manic symptoms (see FIG. 2), as measured by total score on the MACS, following the administration of pentazocine (F=3.69, df=5, p=0.01).

Figure 2:
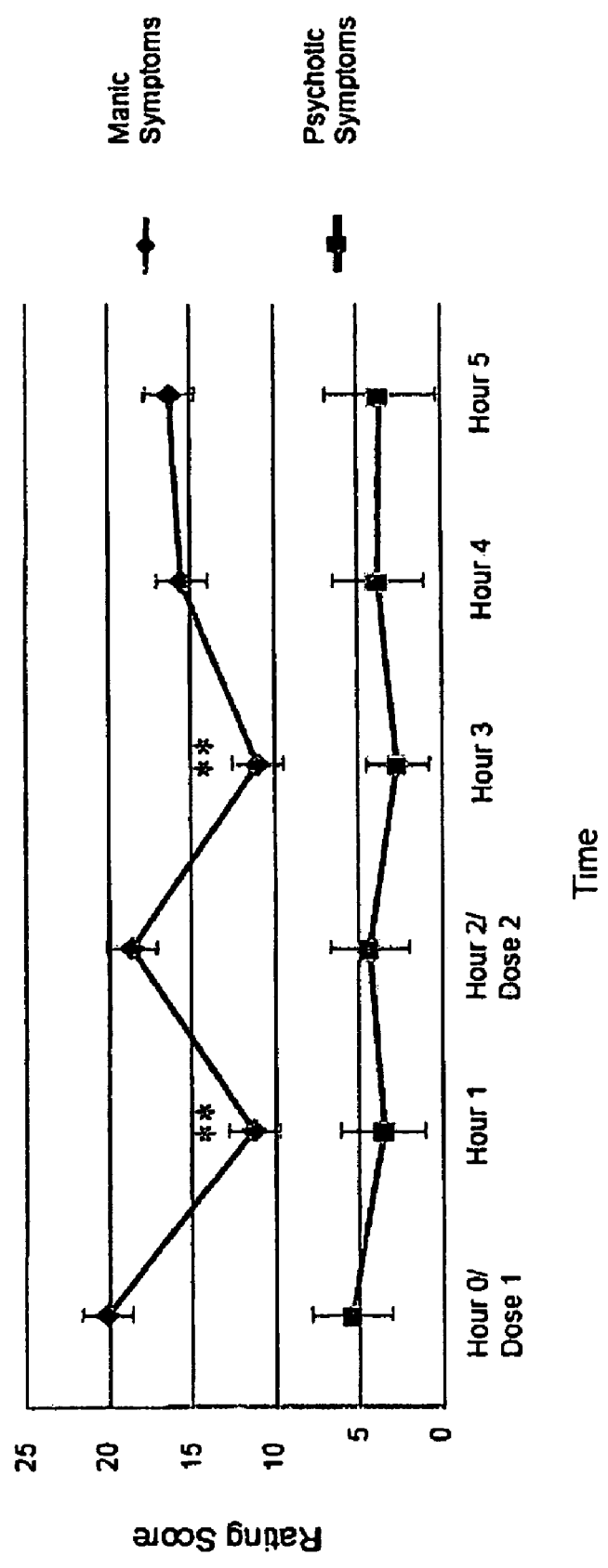
FIG. 2 is a graph showing the effects of pentazocine treatment on mania and psychosis. Subjects were given pentazocine (50 mg by mouth) at Hour 0 (baseline) and at Hour 2. They were given hourly clinician ratings of mania and psychosis using the MACs. All subjects experienced an improvement in manic symptoms, as measured by total score on the MACS, following the administration of pentazocine (F=3.69, df=5, p=0.0.1). Following pentazocine administration, manic symptoms decreased as rated by the Mania. Acute Change Scale (MACS). At one hour after dosing, the mean change in total manic symptom ratings from baseline was −8.8 (from 20.1 to 11.3, or a decrease of 44%). The mean MACS score fell 7.6 points (from 18.6 to 11.0, or 41%) between hour 2, when the second dose was given, and hour 3 (**=0.01). There were no significant changes in psychosis.
Figure 3:
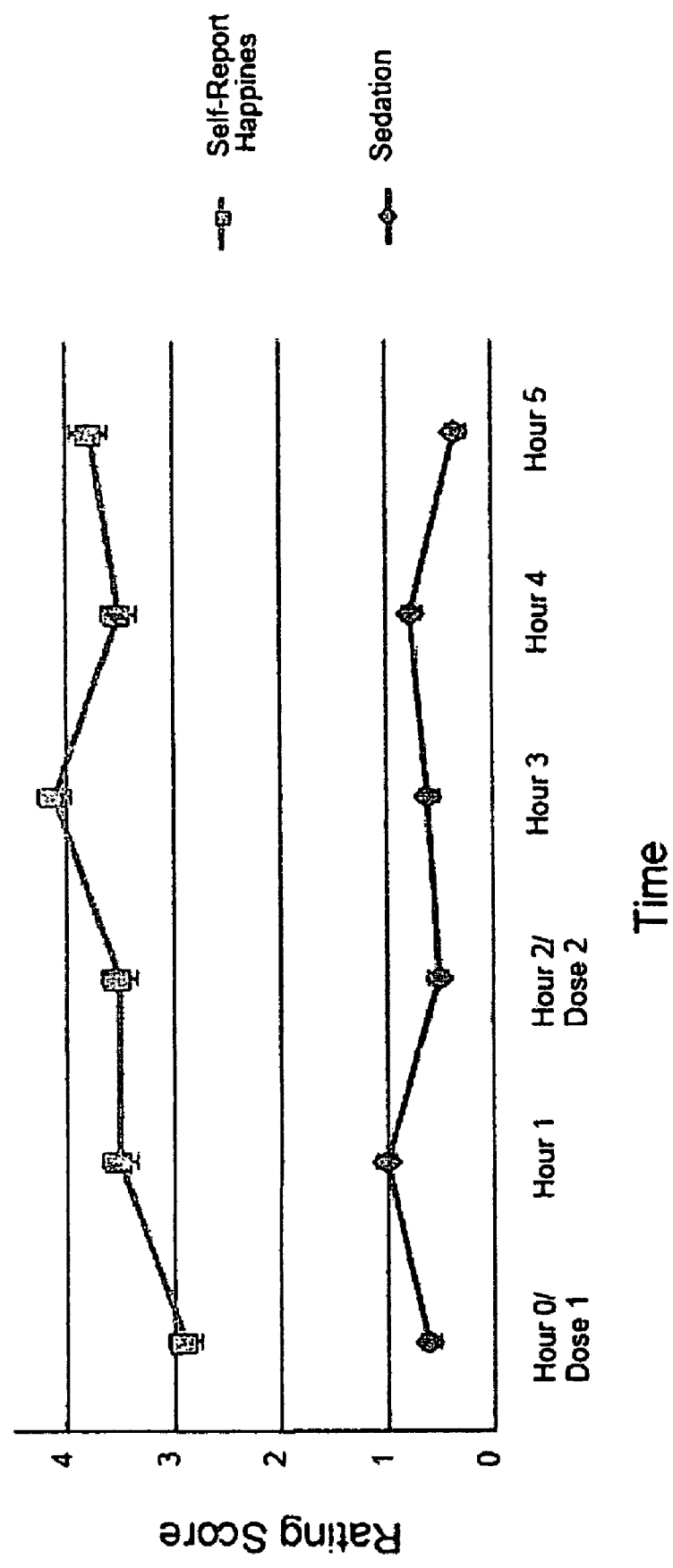
FIG. 3 is a graph showing the effects of pentazocine administration on sedation and mood. Subjects were given pentazocine (50 mg by mouth) at Hour 0 (baseline) and at Hour 2. They were given hourly clinician ratings of reported and observed sedation (on a scale of 0-4). Subjects also completed self-ratings of mood items, including feelings of happiness and sadness (each rated on a Likert-scale of 0-5). There were mild (half-point), nonsignificant, increases in sedation following the first dose of pentazocine. No dysphoria was reported with pentazocine and there was a small and non-significant trend towards an increase in reports of happy mood.

No subject experienced exacerbation of psychotic symptoms and most subjects experienced a mild improvement in psychotic symptoms that mirrored the improvement in manic symptoms (see FIG. 2, F=3.59, df=5, p=0.012). There were no differences in PRN medication use over the three days of the study (pretreatment day=0.8 doses/patient; study day=0.5 doses/patient, p=0.3; post-treatment day=0.3 doses/patient, p=0.6). None of the subjects complained of dysphoria and there were no consistent changes in self-ratings of mood (FIG. 3). Clinician ratings of mood and affect items alone had a trend towards improved mood but this change was not statistically significant during the five hours following administration of pentazocine (F=1.4, df=5, p=0.25). Sedation was low and changes in ratings of sedation were not significant over the course of the treatment day (FIG. 3; F=1.29, df=5, p=0.29).

Over the three days of the study, YMRS scores improved daily (pretreatment day YMRS mean=23.6+8.9; treatment day YMRS mean=22.0+6.9; post-treatment day YMRS mean=12.7+8.4). There was a more substantial improvement between the treatment and post-treatment days than would be anticipated by the difference between the pre-treatment and morning of treatment scores (YMRS on pretreatment vs. treatment day: p=0.4; YMRS on treatment vs. post-treatment day: p=0.01). Thus, there was no evidence of a rebound in symptoms after treatment.

Discussion

Across all subjects, administration of pentazocine was associated with a transient but substantial and statistically significant reduction in manic symptoms. This effect did not appear to be due to sedation. No adverse effects, including psychotomimetic effects, were observed or reported.

Only an acute effect, or two doses, was studied. Nonetheless, these initial results suggest kappa agonists can be used to lower mood.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating mania in a human subject in need thereof, said method consisting of administering to said subject an effective amount of a pharmaceutical composition, said pharmaceutical composition comprising active ingredients and inactive ingredients, said active ingredients consisting of pentazocine, or a pharmaceutically acceptable salt thereof, and optionally naloxone.

2. The method of claim 1, wherein said subject is diagnosed with bipolar disorder, acute mania, or chronic mania.

3. The method of claim 1, wherein said mania occurs in a single episode or is recurring.

4. A method for treating bipolar disorder in a human subject in need thereof, said method consisting of administering to said subject an effective amount of a pharmaceutical composition, said pharmaceutical composition comprising active ingredients and inactive ingredients, said active ingredients consisting of pentazocine, or a pharmaceutically acceptable salt thereof, and optionally naloxone.

5. A method for stabilizing the mood of a human subject diagnosed with a mood disorder, said method consisting of administering to said subject an effective amount of a pharmaceutical composition, said harmaceutical composition comprising active ingredients and inactive ingredients said active ingredients consisting of pentazocine, or a pharmaceutically acceptable salt thereof, and optionally naloxone.

6. The method of claim 1, 4, or 5, wherein said pentazocine is substantially pure (−) pentazocine, or a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,884,077 B2 | Page 1 of 1 |
| APPLICATION NO. | : 12/229841 | |
| DATED | : February 8, 2011 | |
| INVENTOR(S) | : Cohen et al. | |

It is certified that error appears in the above-identified patent and that said Letters Patent is hereby corrected as shown below:

Cover Page, under OTHER PUBLICATIONS, in Cohen et al., replace "Neuropsycopharmacology" with --Neuropsychopharmacology--;

Under OTHER PUBLICATIONS, in Zhu et al., replace "Poteencies" with --Potencies--.

Column 1, Line 57, replace "carbamezapine" with --carbamazepine--.

Column 4, Line 52, replace "psychologic" with --psychological--.

Column 10, Line 45, replace "harmaceutical" with --pharmaceutical--.

Line 45, replace "inactive ingredients said" with --inactive ingredients, said--.

Signed and Sealed this

Thirty-first Day of January, 2012

David J. Kappos
*Director of the United States Patent and Trademark Office*